(12) United States Patent
Root

(10) Patent No.: US 6,217,537 B1
(45) Date of Patent: Apr. 17, 2001

(54) OMNIDIRECTIONAL ARM AND WRIST SUPPORT

(76) Inventor: Warren N. Root, 24921 Muirlands, Unit 112, Lake Forest, CA (US) 92630

( * ) Notice: Subject to any disclaimer, the term of this patent is extended or adjusted under 35 U.S.C. 154(b) by 0 days.

(21) Appl. No.: 09/258,664

(22) Filed: Feb. 26, 1999

Related U.S. Application Data

(63) Continuation-in-part of application No. 09/042,516, filed on Mar. 16, 1998, now Pat. No. 5,876,362.

(51) Int. Cl.⁷ .......................................................... A61F 5/00
(52) U.S. Cl. ................................ 602/21; 400/715; 84/469
(58) Field of Search ........................ 602/20, 21; 400/715; 84/328, 465, 467–469; 601/40

(56) References Cited

U.S. PATENT DOCUMENTS

| 591,800 | 10/1897 | Finnblade et al. . |
|---|---|---|
| 679,288 | 7/1901 | Bohrer . |
| 3,782,719 | 1/1974 | Kuhlman . |
| 5,082,258 | 1/1992 | Niks . |
| 5,876,362 | 3/1999 | Root . |

Primary Examiner—Michael A. Brown
(74) Attorney, Agent, or Firm—Knobbe, Martens, Olson & Bear, LLP

(57) ABSTRACT

A support system for a user of a computer keyboard or for a person performing other manual tasks of extended duration includes a pair of supports which are positioned proximate to respective ends of the keyboard. A rod is supported between the pair of supports to provide a horizontal guide rail. A pair of trolleys support a pair of independently moveable cradles. Each cradle supports a portion of a user's lower arm, wrist and hand. When the user places his or her lower arms, wrists and hands in the cradles, the hands and lower arms are supported above the keyboard or other work surface so that the user is assisted in supporting the weight of his or her arms and hands. The cradles can be moved horizontally from left to right and vice versa as well as arcuately as the user's hands are moved closer to and farther from the user's body. Thus, the user is able to move his or her hands freely over the computer keyboard or other work surface even if the user does not have sufficient muscle tone to adequately support his or her arms for extended duration.

17 Claims, 15 Drawing Sheets

OMNIDIRECTIONAL ARM AND WRIST SUPPORT

RELATED APPLICATIONS

This application is a continuation-in-part of U.S. patent application Ser. No. 09/042,516, filed on Mar. 16, 1998 (U.S. Pat. No. 5,876,362 issued on Mar. 2, 1999).

BACKGROUND OF THE INVENTION

1. Field of the Invention

The present invention is in the field of devices which support the lower arm, wrists and hands during the performance of repetitive tasks such as typing, data entry, parts assembly, or the like.

2. Description of the Related Art

Many personal and job-related tasks involve the use of computer keyboards, calculators and other data entry devices which require a person to have his or her arms and hands extended in front of the person's body for long durations. In addition, other tasks, such as assembly work, sewing, needlework, knitting, painting, or the like, require the arms and hands to be likewise extended. As a result of repeated periods of arm and hand extension, many persons have developed injuries such as carpal tunnel syndrome. In addition, because of aging, accidents, or certain diseases, some persons no longer have the ability to perform relatively simple tasks which require arm and hand extension. A number of devices have been developed to reduce the effects of such extension. For example, wrist pads are available to place in front of a keyboard to elevate the wrists and thereby change the angle of the hands with respect to the keyboard. Such wrist pads do not however assist the user when the user has to move his or her hands from side-to-side on the keyboard. In particular, if a person has weak muscles or the like, the person may be unable to move freely about the keyboard. Thus, additional assistance for using keyboards and for performing other tasks requiring arm and hand extension is desirable.

SUMMARY OF THE INVENTION

The present invention provides a free floating support system which is designed to support the arms and hands during prolonged tasks which require the arms and hands to be extended over a keyboard or other work surface. The system allows freedom of movement over the entire keyboard or work surface while providing full support for the arms and hands. The system is ideal for computer keyboards, typewriters, calculators, and horizontally disposed musical instruments (e.g., pianos and electronic keyboards). In addition, the system provides support while performing tedious assembly work, as well as while doing needlework, sewing, painting, and the like.

One aspect of the present invention is a system for supporting a hand of a user when performing manual tasks above a work surface. The system comprises a horizontally disposed guide rail supported a predetermined distance above the work surface. At least one trolley is positioned on the guide rail. The trolley provides horizontal movement along the guide rail and provides arcuate movement about the guide rail. A cradle is suspended from the trolley. The cradle is sized to support a user's hand, wrist and a portion of the lower arm above the surface. The cradle permits horizontal movement of the user's hand parallel to the guide rail and permits arcuate movement of the user's hand around the guide rail. Preferably, the guide rail is a round rod. Also preferably, the trolley comprises a linear bearing. Alternatively, the trolley comprises a flanged wheel.

Another aspect of the present invention is a system for supporting the hands of a user above a work surface such that the user can freely move the hands with respect to the work surface. The system comprises a first end support and a second end support to position a horizontally disposed guide rail above the work surface. A first trolley and a second trolley are positioned on the guide rail for horizontal movement thereon. A first cradle is suspended from the first trolley beneath the guide rail. The first cradle is positioned to support the user's left hand and left wrist and a portion of the user's lower left arm above the work surface. The first cradle moves horizontally with horizontal movement of the first trolley. The first cradle moves arcuately with respect to the guide rail. A second cradle is suspended from the second trolley beneath the guide rail. The second cradle is positioned to support the user's right hand and right wrist and a portion of the user's lower right arm above the work surface. The second cradle moves horizontally with horizontal movement of the second trolley. The second cradle moves arcuately with respect to the guide rail. Preferably, the rail is round, and the trolleys roll along the length of the rail and slide around the periphery of the rail. In particularly preferred embodiments, the trolleys are linear bearings. Alternatively, the trolleys comprises flanged wheels. Also preferably, the position of the cradle above the work surface is adjustable.

Another aspect of the present invention is a system which supports the hands of a user above a work surface. The system comprises a first support and a second support to position a horizontal guide rail above a work surface between the two supports. The guide rail has an outer periphery. A first trolley and a second trolley are positioned on the guide rail. The trolleys move along the guide rail and slide about the periphery of the guide rail. A first cradle is suspended from the first trolley and a second cradle is suspended from the second trolley. The first and second cradles move longitudinally below the guide rail and move arcuately about the guide rail. Each of the first and second cradles comprises a first portion to support a portion of the lower arm of a user and comprises a second portion extending from the first portion to support the wrist and hand of the user. Preferably, the first support and the second support are adjustable to vary the position of the horizontal rail above the work surface. Also preferably, the first support and the second support are adjustable to vary the horizontal position of the horizontal rail with respect to an edge of the work surface.

Another aspect of the present invention is a system for supporting a hand of a user when performing manual tasks above a computer keyboard. The system comprises a horizontally disposed guide rail supported above the computer keyboard. At least one trolley is positioned on the guide rail. The trolley provides horizontal movement along the guide rail and provides arcuate movement about the guide rail. A cradle is suspended from the trolley. The cradle is sized to support a portion of a user's hand, wrist and lower arm above the computer keyboard. The cradle has side portions to constrain a portion of the user's lower arm therebetween. The cradle has an extended forward portion to support the user's wrist and hand. The cradle permits horizontal movement of the user's hand parallel to the guide rail and permits arcuate movement of the user's hand around the guide rail.

BRIEF DESCRIPTION OF THE DRAWINGS

The present invention will be described below in connection with the accompanying drawing figures in which.

DETAILED DESCRIPTION OF THE PREFERRED EMBODIMENT

As illustrated in FIGS. 1–4, the wrist support system in accordance with the first embodiment of the present invention comprises two vertical end supports 2, 3 at each end of a horizontally disposed tracking rod or overhead rail 1. In the illustrated embodiment, the tracking rod 1 comprises a standard plated steel rod, or the like, to provide a substantially non-bending span between the two end supports 2, 3. For example, the rod 1 may advantageously be ⅜ inch in diameter. The rod 1 is preferably threaded at each end. The rod 1 is fastened at each end by two nuts 4, 5, and 6, 7, respectively, with one nut being on each side of the respective tops of the end supports 2, 3.

Figure 1:
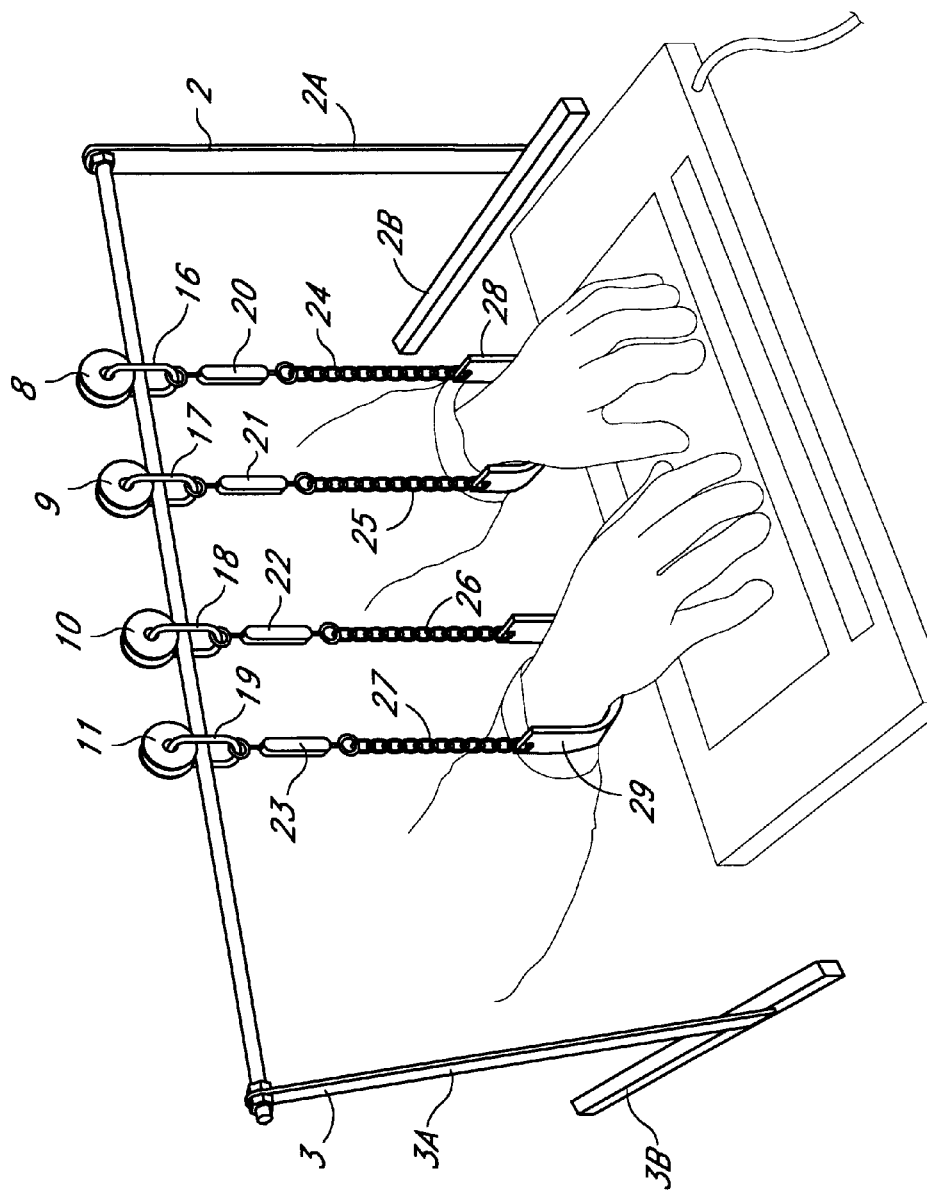
FIG. 1 illustrates a perspective view of a first embodiment of the present invention when being used to support a person's arms and hands over a keyboard.
Figure 2:
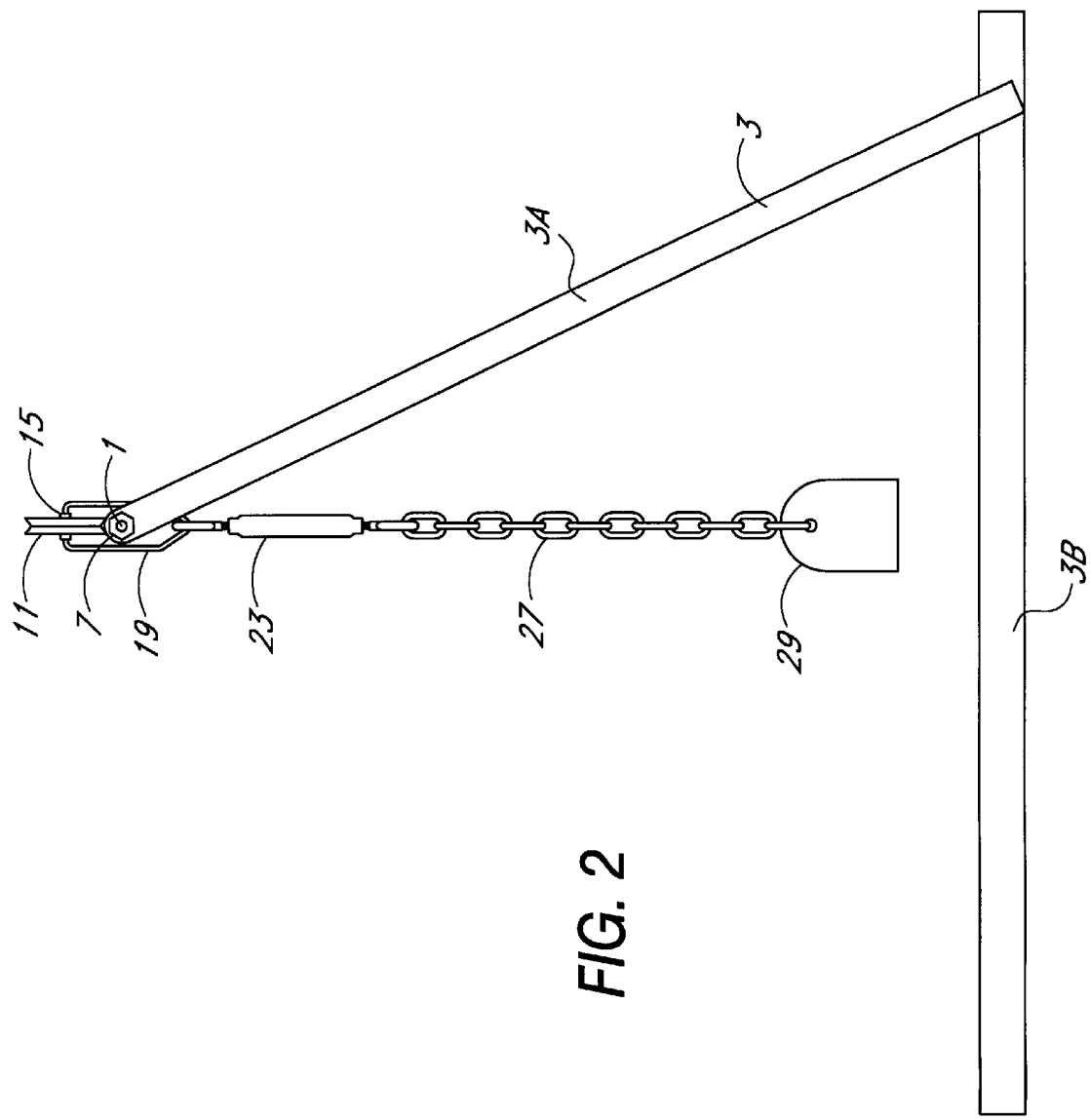
FIG. 2 illustrates a side elevational view of the first embodiment of the present invention showing one of the side supports and illustrating the suspension of the wrist cradle beneath the overhead rail.
Figure 3:
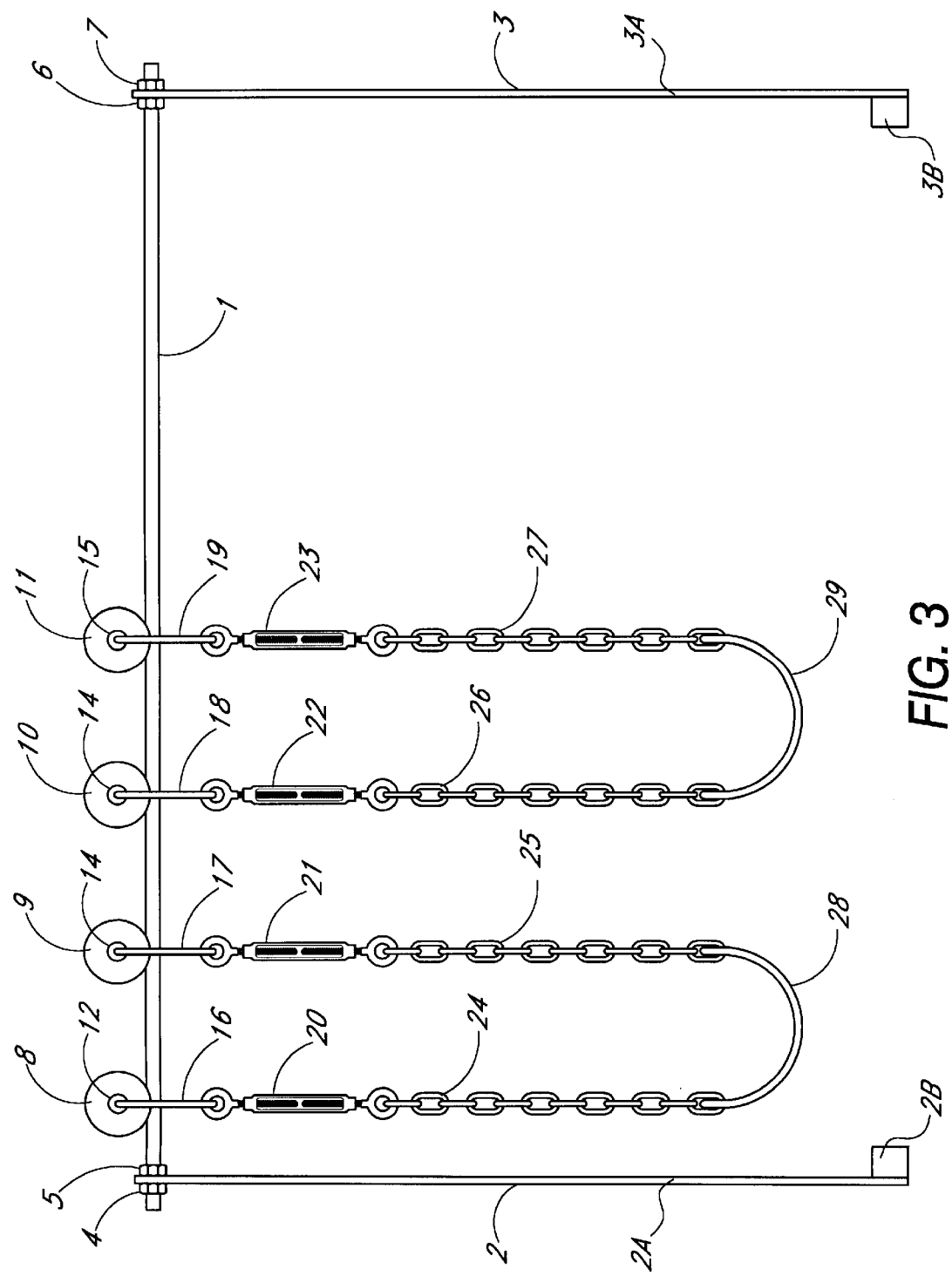
FIG. 3 illustrates a plan view of the first embodiment of the present invention showing the overhead rail in more detail and showing the trolley wheels which provide free left-to-right and front-to-back swinging movement of the wrist cradles.

In the preferred embodiment, the end supports have respective first portions 2A, 3A which are positioned at an angle with respect to vertical, and the bottoms of the end supports are directed away from the user (see FIG. 1). The end supports have respective second portions 2B, 3B, which provide stable horizontal platforms for the for the first portions 2A, 3A when the system is positioned on a desk or the like. As illustrated in FIG. 2, the tracking rod 1 is positioned substantially over the centers of the second portions 2B, 3B so that the system is very stable and does not rock during use. Preferably, the second portions 2B, 3B include cushioned pads (not shown) or the like to inhibit sliding of the second portions 2B, 3B on a desktop or other working surface.

The end supports 2, 3 are spaced apart by a distance slightly less than the length of the tracking rod 1 (i.e., by the length of the tracking rod 1 less the lengths of the two threaded ends extending through and beyond the end supports 2, 3). The length of the tracking rod 1 is selected so that the end supports 2, 3 are positioned outside the working area. For example, when the system is used with a conventional computer keyboard having a width of approximately 18 inches, the tracking rod 1 advantageously has a length of 24–30 inches to accommodate the full width of the keyboard as well as a mouse pad, if desired. For packaging purposes, the tracking rod 1 can be provided in two sections (not shown) with one section having an outside threaded portion (not shown) and the other section having a tapped threaded portion.

The tracking rod 1 supports four grooved wheels 8, 9, 10, 11 which roll on the top side of the tracking rod 1 and thus roll along a straight line substantially parallel to a desktop or other surface on which the system is positioned. The center of each of the grooved wheels 8, 9, 10, 11 includes a sleeve bearing 12, 13, 14, 15. Each sleeve bearing 12, 13, 14, 15 has a hole through its respective center. A respective wire loop 16, 17, 18, 19 passes through the hole in each of the four sleeve bearings 12, 13, 14, 15. Each of the four wire loops 16, 17, 18, 19 straddles and extends below the tracking rod 1, preferably without touching the tracking rod 1, or at least not applying significant pressure on the tracking rod 1 so as to avoid significant frictional contact.

Below the tracking rod, each of the four loops 16, 17, 18, 19 has a respective turnbuckle 20, 21, 22, 23 attached to it such that each turnbuckle is disposed in a generally vertical position below the tracking rod 1 when the system is not in use. A respective chain 24, 25, 26, 27 is attached to the lower end of each of the four turnbuckles 20, 21, 22, 23. The four chains 24, 25, 26, 27 are paired, and each pair of chains 24, 25 and 26, 27 is attached to a respective wrist cradle 28, 29. In particular, the chains 24, 25 support the left wrist cradle 28, and the chains 26, 27 support the right wrist cradle 29. Together, the chains 24, 25, 26, 27 and the turnbuckles 20, 21, 22, 23 permit the wrist cradles 28, 29 to be positioned at any distance below the tracking rod 1 to accommodate different working environments and different personal preferences. For example, links can be removed from or added to the chains for gross adjustment, and the turnbuckle rotated for fine adjustment. It should be understood of course that other suspension devices, such as, for example, string, line or wire, can be used to support the wrist cradles 28, 29.

The wrist cradles 28, 29 may be of any suitable material which provides a reasonable range of flexibility to accommodate different sizes of wrists without being too flexible such that the wrist cradles wrap around the wrists and bind the wrists. For example, in a prototypical embodiment, an arcuate portion of a large diameter automotive rubber hose was found to provide adequate flexibility and support. It is anticipated that many plastic materials will be suitable for the wrist cradles.

Figure 4C:
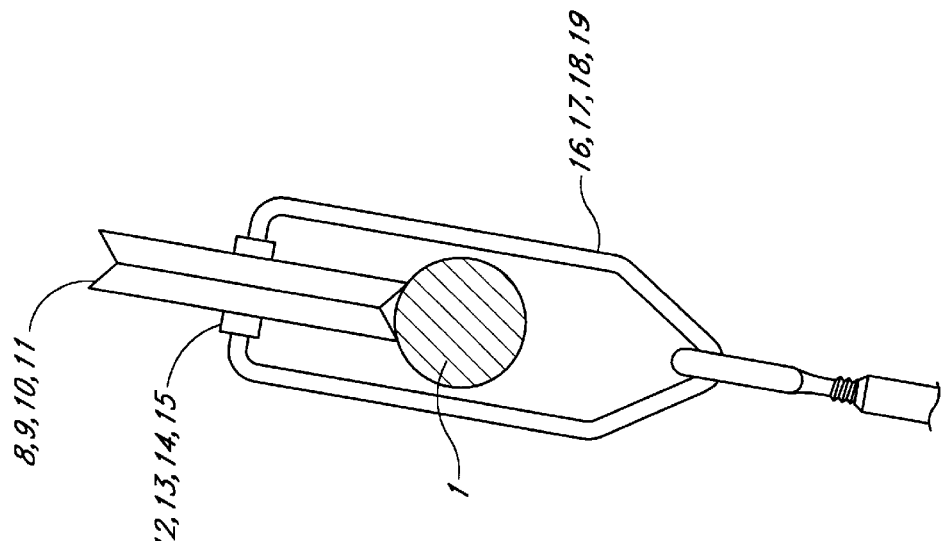
FIGS. 4A, 4B and 4C illustrate cross-sectional views of the overhead rail showing the placement of a trolley wheel on the rod so that the trolley wheel can roll on the rod for left-to-right movement (as viewed in FIG. 3) as well as pivot on the rod to provide front-to-back swinging movement.
Figure 4B:
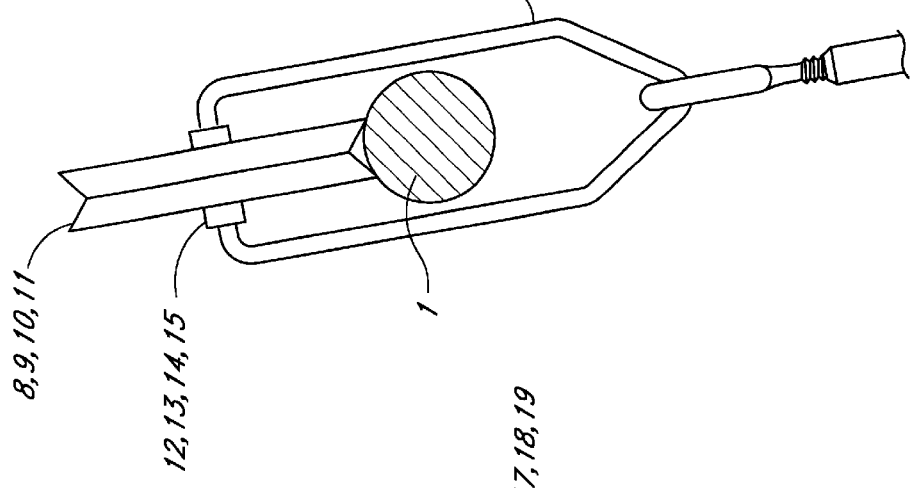
Figure 4A:
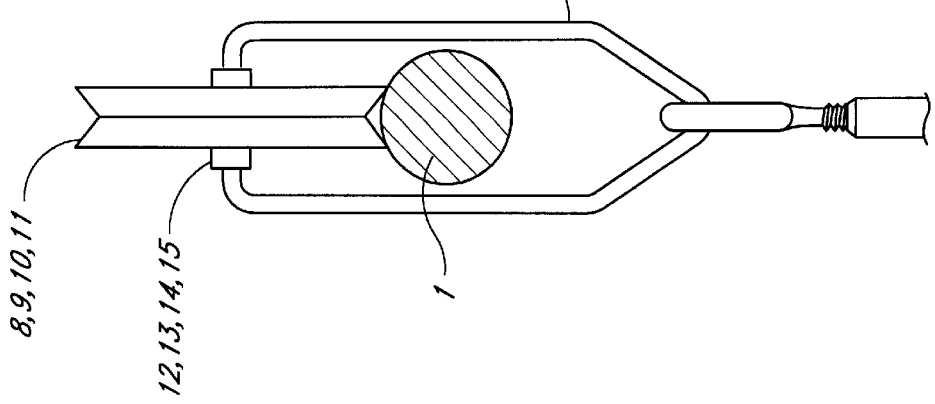

The grooved wheels 8, 9, 10, 11 greatly reduce friction and allow omnidirectional motion of the wrist cradles 28, 29. When the wrist cradles 28, 29 are moved from left to right and from right to left horizontally (as viewed by the user in FIG. 1 or in FIG. 3), the wheels 8, 9, 10, 11 roll along the top of the tracking rod 1 along a generally horizontal line. Absent movement by the user, the wrist cradles 28, 29 hang directly below the tracking rod 1 as illustrated by the position of the loop 16, 17, 18, 19 in FIG. 4A. When the wrist cradles 28, 29 are moved toward the user and away from the user (FIG. 1), the wheels 8, 9, 10, 11 pivot around the circumference of the tracking rod 1 as indicated in FIGS. 4B and 4C (i.e., the wheels 8, 9, 10, 11 move arcuately about the tracking rod 1). By using flanged wheels 8, 9, 10, 11, as illustrated in FIGS. 4A–4C, the frictional contact with the tracking rod 1 is very low so that the wheels 8, 9, 10, 11 freely pivot on the tracking rod 1. The wheels readily roll and pivot simultaneously so that the cradles can move left or right at the same time as the cradles move forward or backward. Thus, for example, a user can readily move his or her hand from a key at the left end of the lowest row of the keyboard to a key at the right end of the highest row of the keyboard in one easy movement. In the illustrated embodiment, the wheels 8 and 9 are not coupled and may move independently with respect to each other. Similarly, the wheels 10 and 11 are not coupled and may move independently with respect to each other. In alternative embodiments, the wheels 8 and 9 may be coupled together and the wheels 10 and 11 may be coupled together so that a substantially constant spacing is maintained between the wheels in each pair of wheels.

When using a conventional keyboard having a sloped key layout, it is anticipated that the cradles 28, 29 will be positioned over the keyboard such that the fingers of a user's hand will be generally proximate to the lower row of keys on the keyboard. Then, as the user moves the cradles way from the user's body, the cradles will swing upward so that the user's fingers move up the slope of the keyboard. The four turnbuckles 20, 21, 22, 23 are readily adjusted to change the arc length of the swing of the wrist cradles to compensate for differing keyboard slopes.

Figure 5:
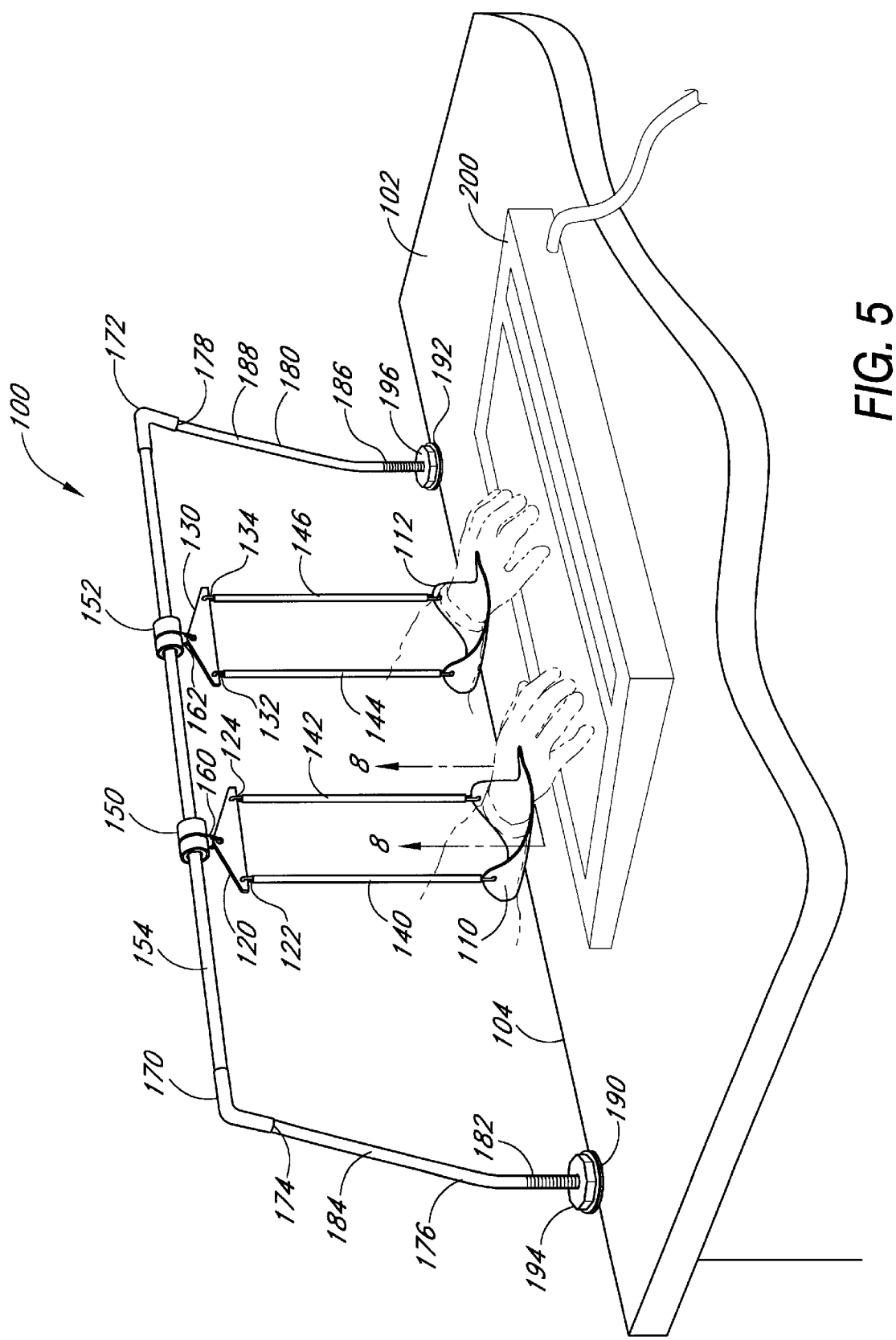
FIG. 5 illustrates an alternative embodiment of the present invention with a desktop mounted support structure, with wrist cradles which provide additional support and with an alternative trolley system.
Figure 6:
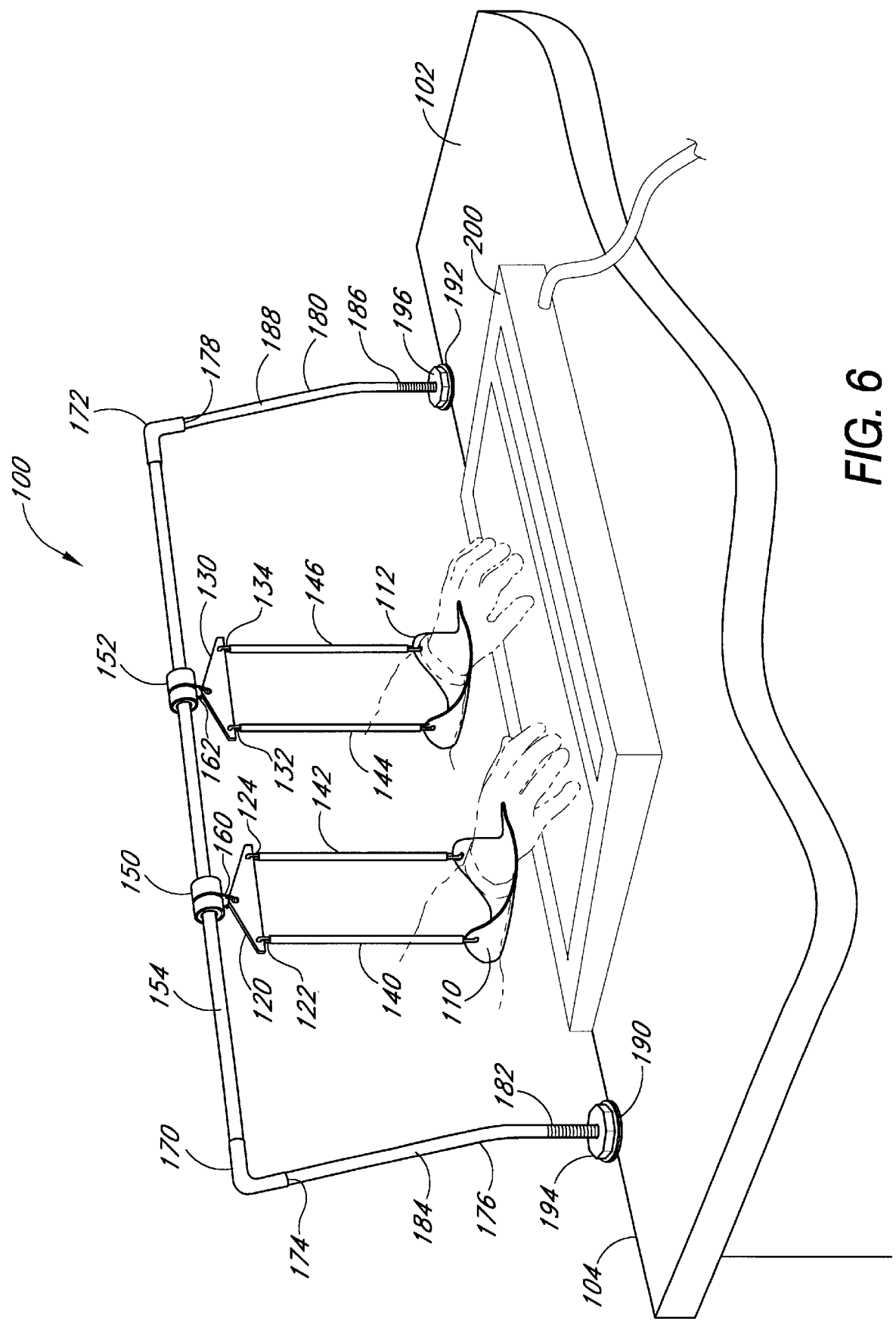
FIG. 6 illustrates the alternative embodiment of FIG. 5 with the support structure reversed to permit a user to place a keyboard closer to the edge of the desktop.

FIGS. 5–15 illustrate further alternative embodiments of the present invention. In particular, FIGS. 5 and 6 illustrate a wrist support system 100 which can be mounted to the edge 104 of a desktop 102.

The embodiment of FIGS. 5 and 6 includes a first cradle 110 for the right wrist and a second cradle 112 for the left wrist. The first cradle 110 is suspended from a first hanger 120 by a first support wire 122 and a second support wire 124. The second cradle 112 is supported from a second hanger 130 by a third support wire 132 and a fourth support wire 134. The first and second support wires 122, 124 pass through respective holes on opposite sides of the first cradle 110. The third and fourth support wires 132, 134 pass through respective holes on opposite sides of the second cradle 112. In the preferred embodiment, the first, second, third and fourth support wires 122, 124, 132, 134 comprise 0.039 inch (1 millimeter) piano wire, or the like, positioned in a respective sleeve 140, 142, 144, 146. The sleeves advantageously comprise silicon plastic tubing, or the like.

Figure 7:
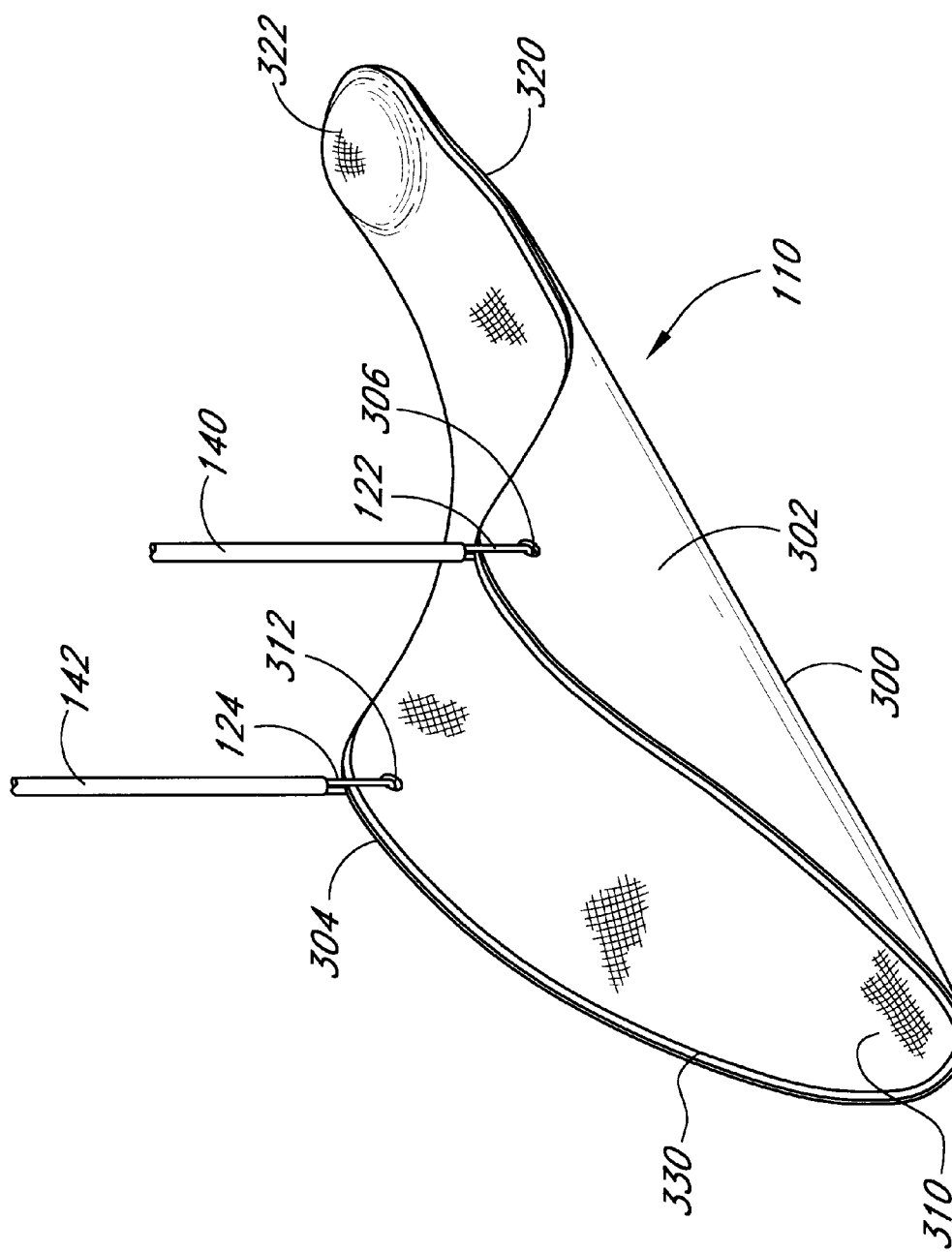
FIG. 7 illustrates the wrist cradle of FIGS. 5 and 6 in more detail.

As shown in more detail in FIG. 7, the end of each support wire is bent into a generally U-shape to support the cradle, and the free end is passed back into the respective sleeve to preclude the free end from snagging a user's skin or clothing and also to assist in maintaining the U-shape of the support wire.

In alternative embodiments (not shown), the first, second, third and fourth support wires 122, 124, 132, 134 comprise flexible cables, such as, for example, seven-strand braided stainless steel wires from Sevenstrand Corporation, 899 West Cowles Street, Long Beach, Calif. The flexible cables are preferably looped through the holes in the cradles 110, 112 and are clamped at the first and second hangers 120, 130.

In the illustrated embodiment, each of the first and second hangers 120, 130 is generally triangularly shaped with a base and an opposing apex. A U-shaped portion of each of the first and second support wires 122, 124 engages a respective hole at each end of the base of the first hanger 120. A U-shaped portion of each of the third and fourth support wires 132, 134 passes through a respective hole at each end of the base of the second hanger 130. Again, the free end of each support wire at the hangers 120, 130 is passed back into the respective sleeve for the reasons discussed above.

The apex of each of the hangers 120, 122 is suspended from a respective trolley 150, 152 which is mounted on a horizontally disposed guide rod 154. As will be discussed in more detail below in connection with FIGS. 9 and 10, the trolleys 150, 152 comprise linear bearings mounted within a cylindrical plastic shell. A hanger wire 160 supports the first hanger 120 from the trolley 150, and a hanger wire 162 supports the second hanger 130 from the trolley 152.

The horizontal rod 154 advantageously comprises a stainless steel rod having a substantially circular cross section and having a diameter of approximately 0.375 inch (9.5 millimeters). The horizontal rod 154 has a length of approximately 30 inches (76.2 centimeters) between first and second ends.

The horizontal rod 154 is welded or otherwise connected to a first elbow 170 at the first end and to a second elbow 172 at the second end. The first elbow 170 has a tubular portion 174 which receives a first support rod 176. The second elbow 172 has a tubular portion 178 which receives a second support rod 180. Preferably, the first and second support rods 176, 180 comprise steel or aluminum and have solid circular cross sections with diameters of approximately 0.375 inch (9.5 millimeters). The tubular portions 174, 178 of the first and second elbows 170, 172 have inside diameters of approximately 0.375 inch (9.5 millimeters) with sufficient tolerance to removably receive the first and second rods 176, 180.

The first support rod 176 has a generally vertical portion 182 proximate to the desk top 102 and a non-vertical portion 184 disposed at an angle with respect to the vertical portion 182. The second support rod 180 has a generally vertical portion 186 proximate to the desk top 102 and a non-vertical portion 188 disposed at an angle with respect to the vertical portion 186. For example, in the preferred embodiment, the non-vertical portions 184, 188 are disposed at an angle of approximately 20 degrees with respect to the vertical portions 182, 186.

The first support rod 176 is positioned in a first clamp 190, and the second support rod 180 is positioned in a second clamp 192. The clamps 190, 192 are secured to the edge 104 of the desktop 102. A lower portion of the first support rod 176 is threaded and is engaged with a first vertical adjustment knob 194. A lower portion of the second support rod 180 is threaded and is engaged with a second vertical adjustment knob 196. The first vertical adjustment knob 194 rests on the first clamp 190, and the second vertical adjustment knob 196 rests on the second clamp 192. As the first and second vertical adjustment knobs 194, 196 are turned clockwise or counterclockwise, the first vertical support rod 176 and the second vertical support rod 180 are caused to move up or down to thereby adjust the position of the horizontal rod 154 with respect to the desktop 102. Preferably, the adjustment knobs 194, 196 are adjusted so that the rod 154 is level and is a desired distance above the desktop 102. By adjusting the position of the rod 154, it is not necessary to adjust the position of the cradles 110, 112 with respect to the rod 154 in the manner described in connection with the embodiments of FIGS. 1–4. The vertical adjustment knobs 194, 196 are advantageously constructed from PVC or other suitable material (e.g., metal). Preferably, the knobs 194, 196 are constructed in a octagonal shape and are sized to be sufficiently large that the knobs can be easily turned with a user's hand rather than requiring a wrench or other tool.

The non-vertical portions of the support rod 176, 180 permit the horizontal rod 154 to be positioned in two locations over the desktop 102 to allow a user to choose where the user's hands are supported. In FIG. 5, the support rods 176, 180 are oriented with the non-vertical portions 184, 188 directed over the desktop 102 before inserting the support rods 176, 180 into the respective elbows 170, 172. In this orientation, the horizontal rod 154 is positioned over the desktop 102, and the user's hands are positioned inward from the edge 104 of the desktop 102. Thus, the user's hands are positioned over a keyboard 200 which is located on the desktop 102 away from the edge 104 of the desktop 102.

In contrast to the orientation in FIG. 5, the non-vertical portions 184, 188 of the support rods 176, 180 are turned by 180° in FIG. 6 so that the non-vertical portions 184, 188 are directed away from the desktop 102. Thus, in FIG. 6, the horizontal rod 154 is positioned away from the edge 104 of the desktop 102, and the user's wrists and hands are supported over a keyboard 200 which is located at the edge 104 of the desktop 102. Thus, the user has a choice of where to position the keyboard to accommodate individual preferences.

As discussed above in connection with the embodiments of FIGS. 1–4, the trolleys 150, 152 move laterally on the rod 154 to permit lateral movement (i.e., left and right movement) of a user's hands across the keyboard 200. The trolleys 150, 152 also permit forward and backward movement of the user's hands with respect to the rows of the keyboard 200. The use of linear bearings for the trolleys 150, 152 permit a smoother movement and also provide a more compact appearance for the trolleys 150, 152.

Figure 8:
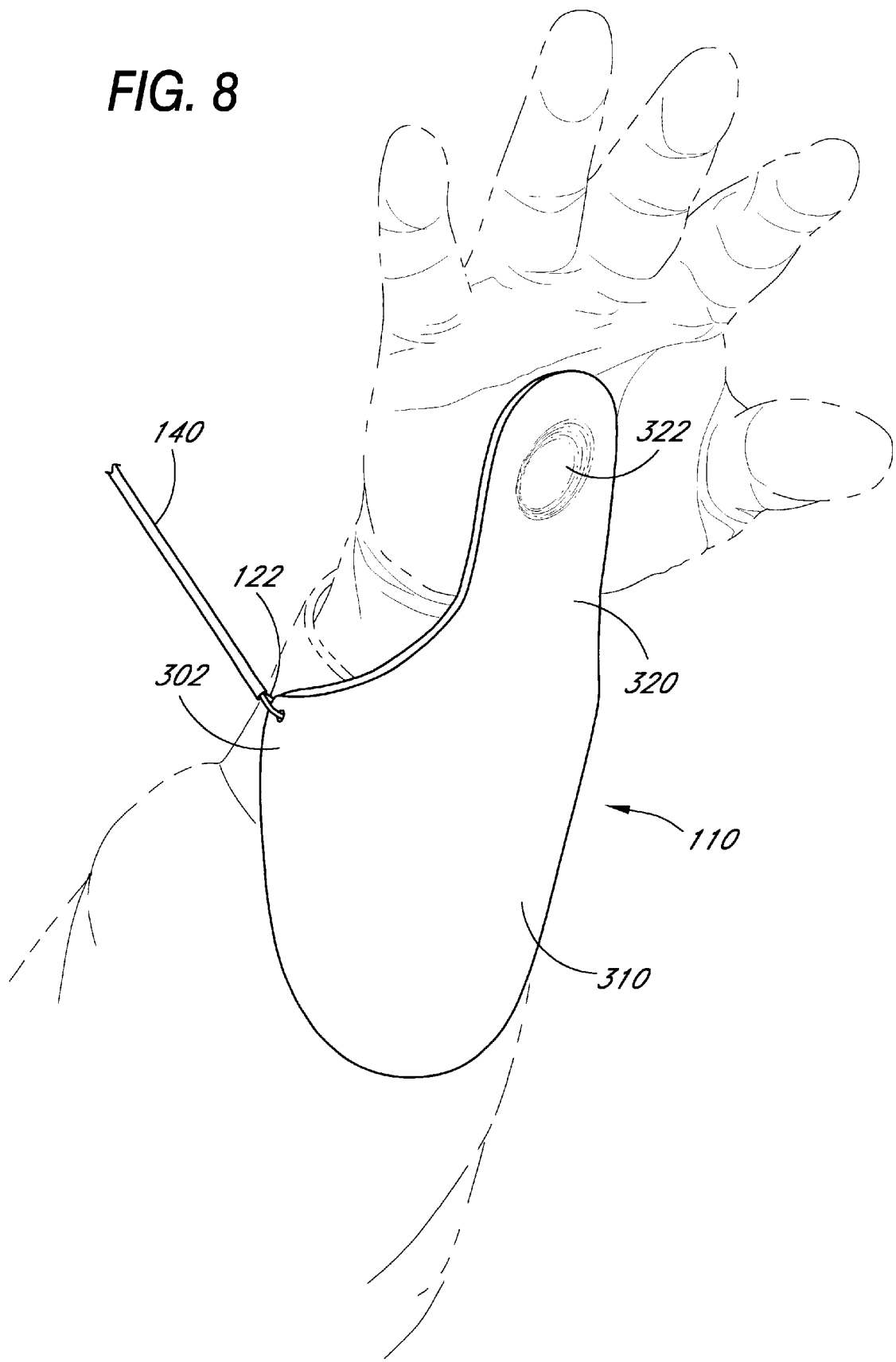
FIG. 8 is a view taken along the lines 8—8 in FIG. 5 which shows the wrist and palm support provided by the wrist cradle.

The first cradle 110 is shown in more detail in FIGS. 7 and 8. The second cradle 112 is preferably interchangeable with the first cradle 110, and the following description also applies to the second cradle 112. As illustrated, the first cradle 110 comprises an outer shell 300 formed in a generally semicircular shape between a first side 302 and a second side 304. The first side 302 and the second side 304 are spaced approximately 4 inches (10.1 centimeters) apart. A first hole 306 in the first side 302 and a second hole 308 in the second side 304 receive the support wires 122 and 124, respectively.

As illustrated in FIG. 8, a portion of the user's lower arm and a portion of the user's wrist are supported by an arcuate bottom portion 310 between the two sides 302, 304. The bottom portion 310 extends forward past the two sides 302, 304 to a generally flat extended portion 320 which supports the user's palm. The flat extended portion 320 may also support a portion of the user's wrist. In the illustrated embodiment, the extended portion 320 has a width of approximately 1.5 inches (3.8 centimeters). Preferably, the extended portion 302 has a raised portion 322 at the end thereof. The raised portion 322 conforms the end of the extended portion 320 with the concave contour of the user's palm to provide additional comfort to the user. The overall length of the cradle 110 in one embodiment is approximately 8.25 inches (21 centimeters).

In the preferred embodiment, the cradle 110 is stamped from aluminum having a thickness of approximately 0.060 inch (1.5 millimeter). The cradle 110 can also be constructed from other materials, such as for example, plastic.

In the preferred embodiment, the inner portion of the cradle 110 in contact with the user's lower arm, wrist and palm is lined with a cushioning material 330. In the preferred embodiment, a 0.125-inch (3.2-millimeter) layer of neoprene material similar to the material used to line wet suits has been found to be particularly advantageous. The neoprene provides cushioning and the nylon cloth liner isolates the neoprene from the user's skin and clothing. The cushioning material 330 is fastened to the cradle 110 with glue or other suitable bonding material with the nylon cloth liner of the cushioning material 330 exposed. Other suitable lining material may also be used.

Figure 10:
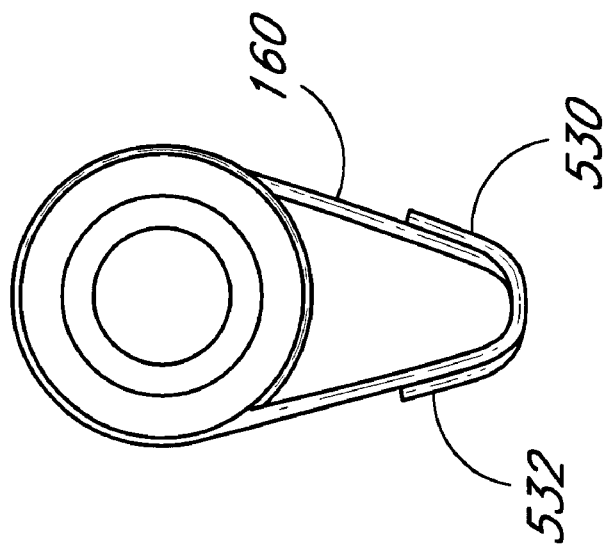
FIG. 10 is elevational view of the linear bearing of the trolley system of FIGS. 5 and 6 showing the placement of the supporting wires on the outer shell of the bearing.
Figure 9:
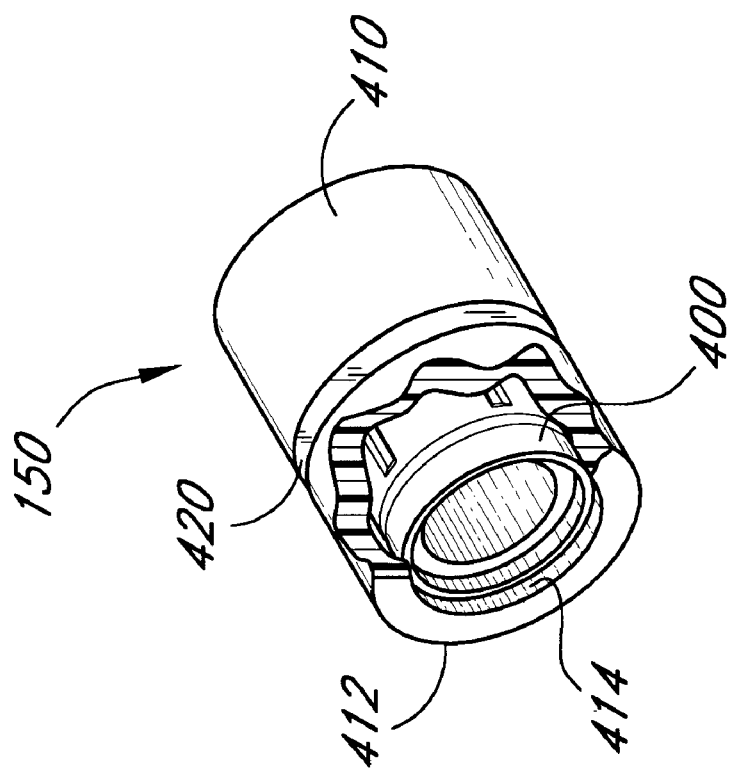
FIG. 9 is an enlarged view with a partial cross section of the linear bearing of the trolley system of FIGS. 5 and 6 showing the inner bearing and the outer shell.

FIGS. 9 and 10 illustrated the first trolley 150 in more detail. The second trolley 152 is substantially similar to the first trolley 150, and the following description also applies to the second trolley 152.

As illustrated in FIG. 7, the first trolley 150 comprises an linear bearing 400. The linear bearing 400 is preferably an IKO Model LBB 6 linear bearing available from IKO Nippon Thompson Co., Ltd., of Tokyo, Japan. The linear bearing 400 has an inner surface having an inside diameter slightly greater than 0.375 inch (9.5 millimeters) so that the linear bearing 400 fits on the rod 154. The construction of the linear bearing 400 is well known. The linear bearing 400 has a plurality of internal bearing races. Each bearing race has a plurality of bearings which run longitudinally along the inner surface of the linear bearing so that the rod 154 is supported by a plurality of bearings. The linear bearing 400 moves freely longitudinally along the rod 154 and also moves freely arcuately about the rod 154.

As further illustrated in FIG. 9, the linear bearing 400 is press-fit into an outer sleeve 410 having an inner surface 412 and an outer surface 414. In the illustrated embodiment, the outer sleeve 410 comprises PVC or other suitable plastic material which has an inner diameter selected to closely match the outer diameter of the linear bearing 400. For example, in the preferred embodiment, the linear bearing 400 has an outer diameter of approximately 5/32 inch (15 millimeters) such that when the linear bearing 400 is press-fit into the outer sleeve 410 having an inner diameter of approximately 5/32 inch, the linear bearing 400 fits snugly in the outer sleeve 410 without deforming the linear bearing 400. If the inner diameter of the outer sleeve 410 is too small, the bearings within the linear bearing 400 may bind such that the linear bearing 400 no longer moves freely on the rod 154.

As further illustrated in FIG. 9, a circumferential groove 420 is cut into the outer surface 414 of the PVC sleeve 410. The groove 420 receives and holds the hanger wire 160.

Preferably, the hanger wire 160 is wound approximately 1¼ times around the outer surface 414 in the groove 120. The two free ends of the hanger wire 160 are formed in first and second J-hooks 530, 532. The two free ends are passed through the upper hole in the first hanger 120 (FIGS. 5 and 6), and the two hooks 530, 532 prevent the first hanger 120 from disengaging from the hanger wire 160.

Figure 11:
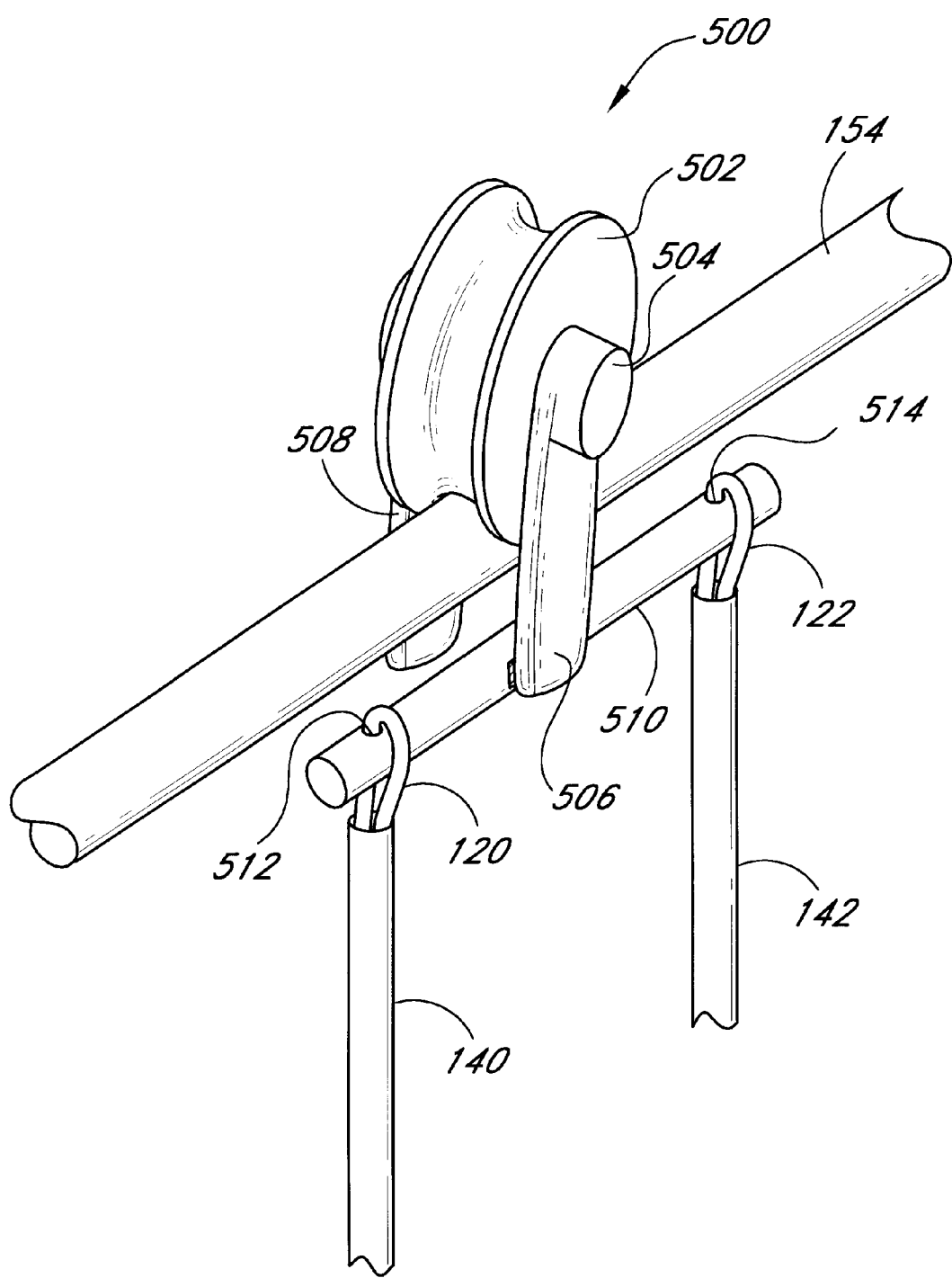
FIG. 11 illustrates a further alternative embodiment of the trolley structure which uses a single flanged wheel to support each wrist cradle.

FIG. 11 illustrates an alternative embodiment of a trolley 500 which can be used in place of the trolley 150 or the trolley 152. The trolley 500 of FIG. 11 uses a grooved wheel 502 which is similar to the grooved wheels 8, 9, 10, 11 of FIGS. 1–4. However, in FIG. 11, only a single wheel 502 is used to support each cradle 110 or 112. An axle 504 passes through the center of the wheel 502 and is connected to a first side bar 506 and to a second side bar 508. The first side bar 506 is fastened to the midpoint of a horizontal hanger 510. The horizontal hanger 510 has first and second ends with a first hole 512 proximate to the first end and a second hole 514 proximate to the second end. When supporting the first cradle 110, the first support wire 122 passes through the first hole 512, and the free end of the support wire 122 is inserted into the end of the sleeve 140, as discussed above. Similarly, the second support wire 124 passes through the second hole 514, and the free end of the second support wire 124 is inserted into the end of the sleeve 142. A second trolley (not shown) for the second cradle 112 has a similar structure.

The second side bar 508 is not fixed to the horizontal hanger 510. Rather, the second side bar 508 is spaced apart from the horizontal hanger 510 by a distance that is slightly less than the diameter of the rod 154. The second side bar 508 is sufficiently resilient to permit the trolley 500 to mounted on the rod 154. Thereafter, the resiliency of the second side bar 508 prevents the trolley 500 from being inadvertently dislodged from the rod 154 until sufficient force is applied in the vertical direction in FIG. 11 to force the rod 154 between the second side bar 508 and the horizontal hanger 510.

FIGS. 12–15 illustrate the first clamp 190 in more detail. The second clamp 192 is substantially similar to the first clamp 190, and the following description also applies to the second clamp 192.

Figure 12:
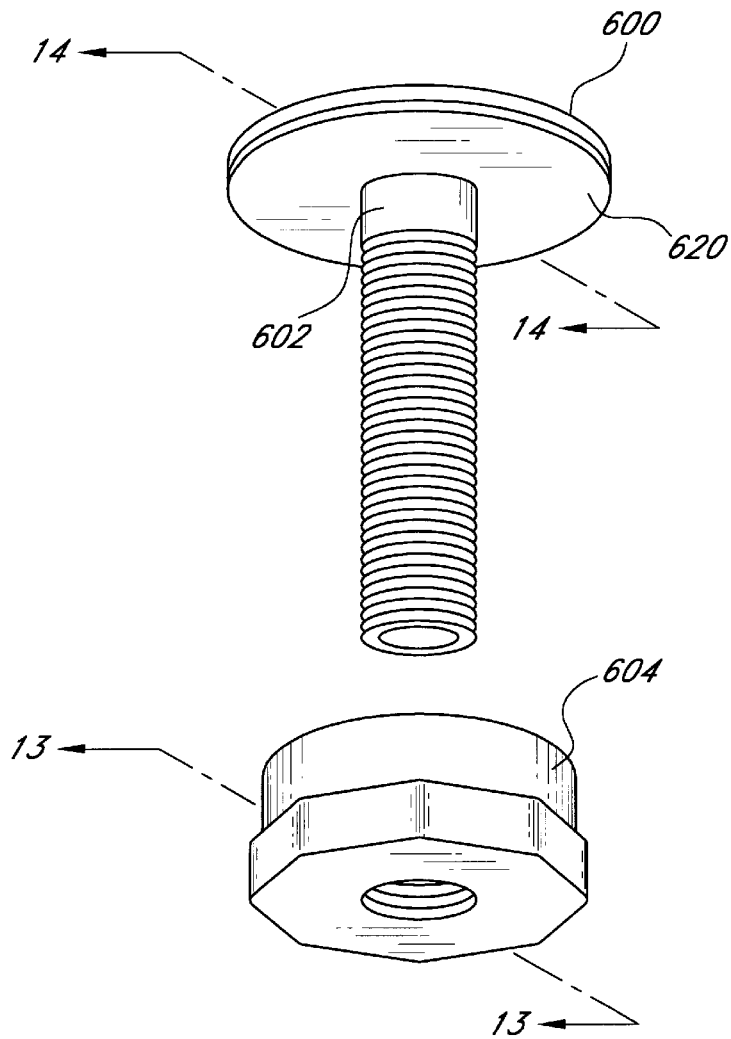
FIG. 12 illustrates the desktop clamp used in the embodiment of FIGS. 5 and 6.
Figure 14:
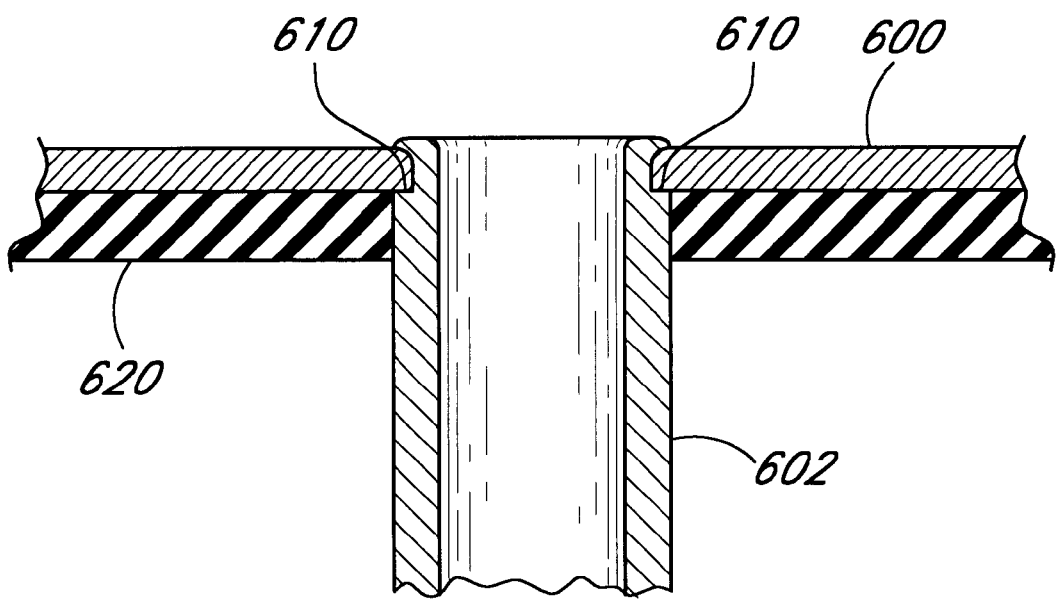
FIG. 14 illustrates a cross-sectional view of the fixed plate of FIG. 12.

As illustrated in FIG. 12, the first clamp 190 comprises an upper fixed head 600, an externally threaded cylindrical shank or stem 602, and an internally threaded knob 604. Preferably, as shown in FIG. 14, the fixed head 600 is swaged or staked onto the stem 602 in a conventional manner. For example, the stem 602 preferably has a lip 610 formed on one end thereof. The fixed head 600 is positioned on the lip 610 with a portion of the stem 602 extending above the fixed head 600. The extended portion is swaged or staked to fix the fixed head 600 to the stem 602.

Preferably, a thin rubber pad 620 is positioned on the stem 602 in contact with the fixed head 600. In the preferred embodiment, both the fixed head 600 and the pad 620 are circular. For example, the fixed head 600 is advantageously a stainless steel washer having a diameter of approximately 1.75 inches (44.4 millimeters).

The stem 602 is a hollow cylindrical tube having an inside diameter of approximately 0.375 inch (9.5 millimeters) to receive the first support rod 176. The stem 602 has an outside diameter of approximately 0.625 inch (15.9 millimeters) and is threaded as shown.

Figure 13:
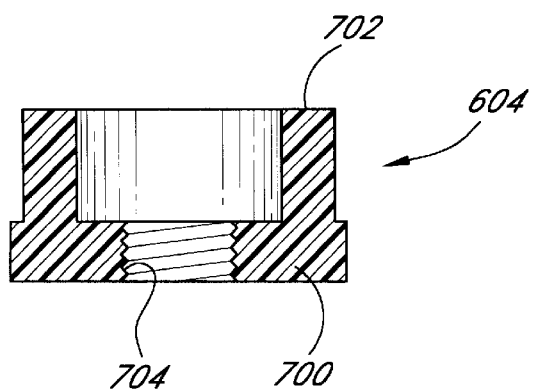
FIG. 13 illustrates a cross-sectional view of the clamping knob of FIG. 12.

As illustrated in cross section in FIG. 13, the knob 604 comprises a solid head portion 700 and a cylindrical body portion 702 constructed from PVC or other suitable metallic or plastic material. The body portion 702 has an outside diameter of approximately 1.75 inches (44.4 millimeters) and an inside diameter of approximately 1.125 inches (28.6 millimeters). The body portion 702 has a cylindrical wall with a thickness of approximately 0.31 inch (7.9 millimeters).

The head portion 700 has a generally octagonal shape so that the head portion 700 can be gripped by hand or with a wrench. In the preferred embodiment, the head portion 700 has a maximum diagonal dimension of approximately 1.875 inches (47.6 millimeters). The head portion 700 is threaded in the center with threads 704 having an outer diameter of approximately 0.625 inch (15.9 millimeters) to match the outer threads of the stem 602.

Figure 15:
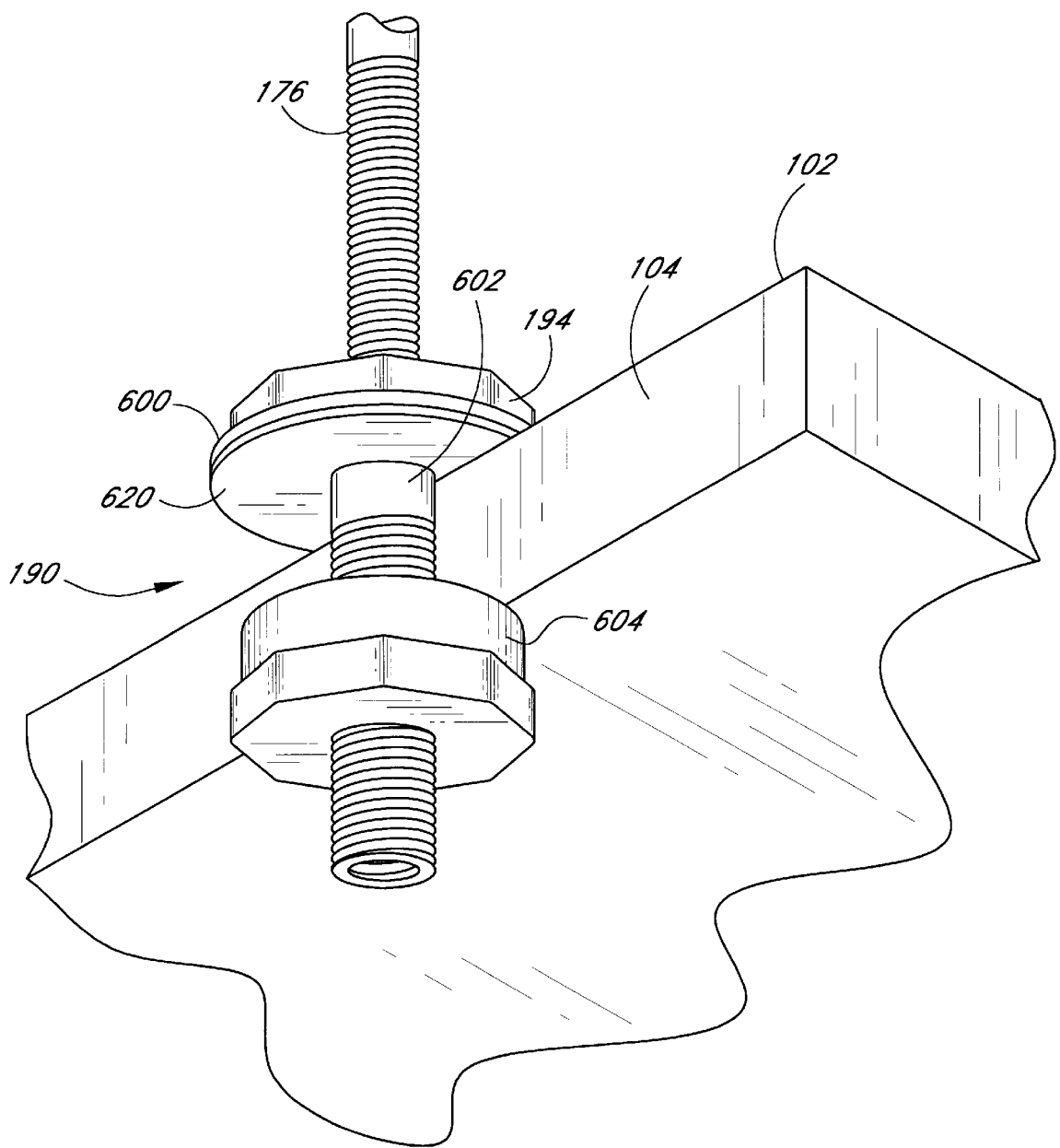
FIG. 15 illustrates the desktop clamp positioned on the edge of a desktop.

As illustrated in FIG. 15, the knob 604 is threaded onto the stem 602 with the edge 104 of the desktop 102 positioned between the pad 620 and the body portion 702 of the knob 604. As the knob 604 is tightened, the pad 620 engages the top of the desktop 102, and the walls of the body portion 702 of the knob 604 engage the bottom of the desktop 102. By using the hollow cylindrical body portion 702 rather than a solid body portion for the knob 604, the force caused by tightening the knob 604 is applied over a smaller surface area of the bottom of the desktop 102. Thus, the clamp 190 can be readily tightened by hand or with minimal use of a wrench.

Figure 16:
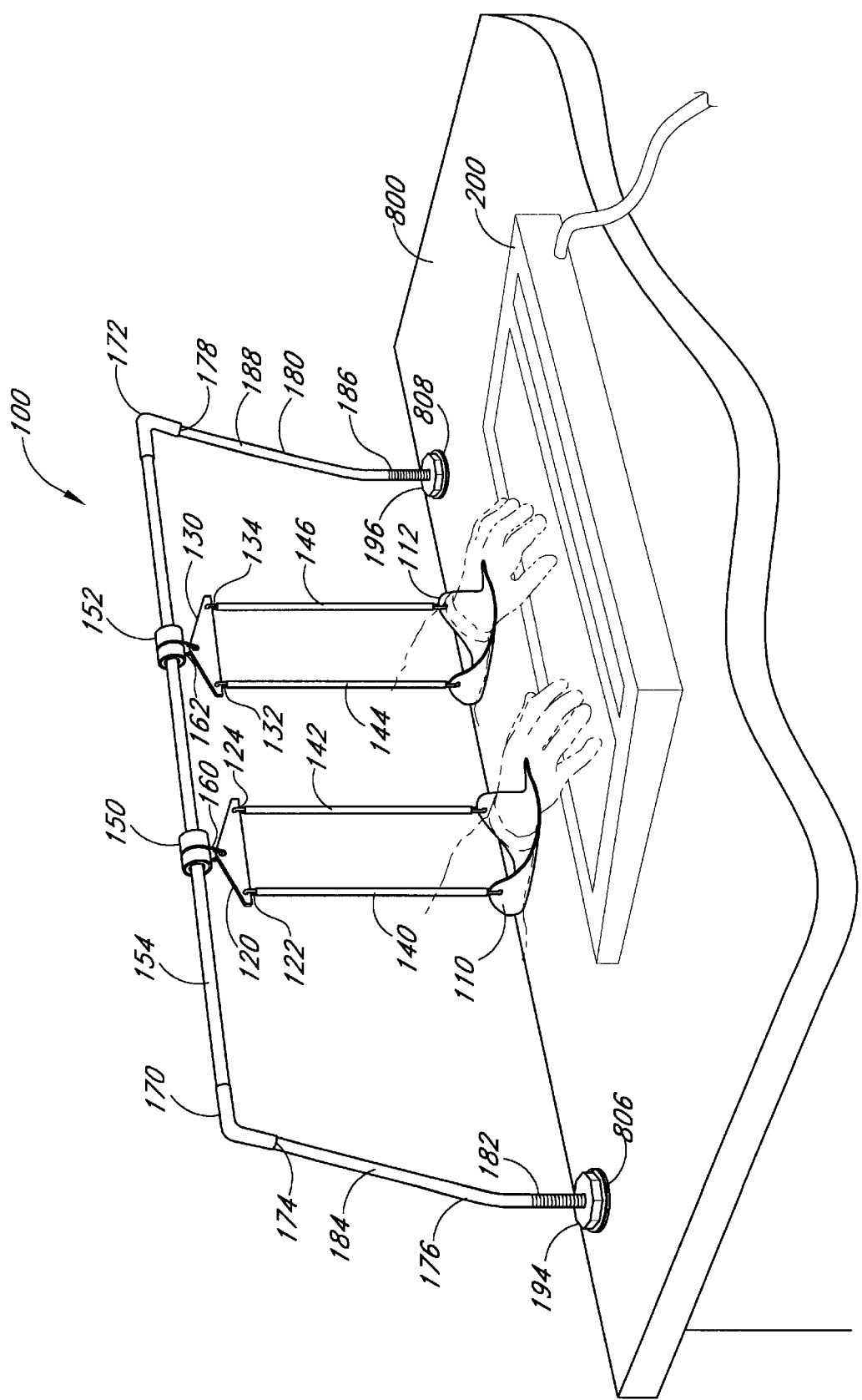
FIG. 16 illustrates an alternative embodiment to the system illustrated in FIGS. 5 and 6 in which the vertical support rods are mounted directly into the desktop or work surface.

FIG. 16 illustrates a further alternative embodiment of the present invention in which a desktop 800 or other workstation surface is modified to include a first hole 802 (FIG. 17) having a first receptacle 806 positioned therein and to include a second hole (not shown) having a second receptacle 808 positioned therein. Each receptacle 806, 808 is sized to receive the first rod 176 and the second rod 180, respectively. As shown in more detail in FIG. 17, in particularly preferred embodiments, the first receptacle 806 in the first hole 802 comprises a stem 810 similar to the stem 602 described above. A fixed head 812 is swaged or staked onto the stem 810, as discussed above. The fixed head 812 advantageously rests on a pad 814. The second receptacle 808 has a similar structure and is not shown in detail.

Figure 17:
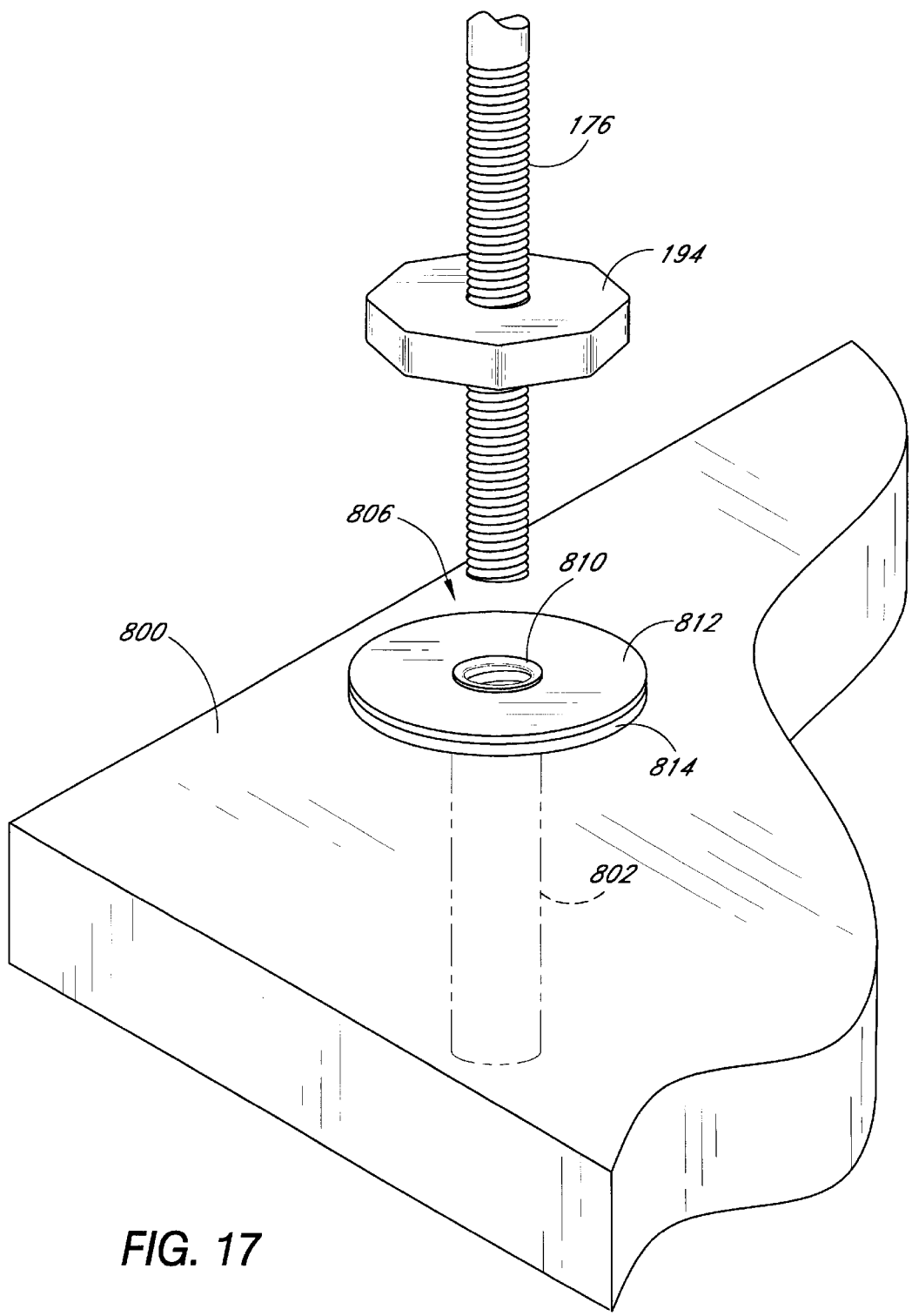
FIG. 17 is an enlarged exploded view of a portion of the desktop of FIG. 16 showing the mounting of the vertical support rod directly into the desktop.

In the embodiment of FIGS. 16 and 17, the forces of the threaded lower portions of the rods 176, 180 are applied against the insides of the stems 810 rather than being applied directly against the material comprising the desktop 800, thus preserving the integrity of the first hole 802 and the second hole (not shown). As discussed above, the knobs 194, 196 on the support rods 176, 180 are rotated to adjust the height of the support rods 176, 180 and thus adjust the height of the horizontal rod 154.

The present system provides a natural resting position for the user's wrists and hands. Thus, for example, when using a computer keyboard in conjunction with a mouse, the present system assists the user in returning from a mouse operation to a keyboard without having to look at the keyboard to determine correct hand placement. Thus, the user can continue to watch the screen when transitioning between the two operations.

It can be readily seen from the foregoing that when the free floating support system in accordance with the present invention is used with keyboards, typewriters, data entry devices, musical instruments, and the like, or is used to assist in the performance of tedious assembly work, the system will greatly reduce stresses and strains to the wrists and arms. The present invention is particularly advantageous for a person having weak muscles such that the person cannot readily support his or her hands above a keyboard or other work surface. The cradles provide the necessary support so that the person's remaining muscular capabilities can be applied to the manipulation of the keyboard or to any other task rather than to the effort of supporting the wrists and hands.

While described in connection with a computer keyboard, it should be understood that the present invention has applicability to other repetitive activities, such as for example, assembly work, wherein a user works in a particular area with his or her hands above a work surface.

While preferred embodiments of this invention have been disclosed herein, those skilled in the art will appreciate that changes and modifications may be made therein without departing from the spirit and scope of the invention as defined in the appended claims.

What is claimed is:

1. A system for supporting a hand of a user when performing manual tasks above a work surface, comprising:

a horizontally disposed guide rail supported a predetermined distance above the work surface, said guide rail having an outer periphery, at least a portion of said outer periphery being arcuate;

at least one trolley positioned on said guide rail in contact with said arcuate portion of said outer periphery, said trolley providing horizontal movement along said guide rail and providing arcuate movement of said trolley about said guide rail; and a cradle suspended from said trolley, said cradle sized to support a portion of a user's hand, wrist and lower arm above said work surface, said trolley permitting horizontal movement of said cradle and the user's hand parallel to said guide rail and permitting arcuate movement of said cradle and the user's hand around said guide rail, said cradle having a first portion for supporting a portion of the user's lower arm and having a second, extended portion for supporting the user's wrist and hand.

2. The system as defined in claim 1, wherein said outer periphery of said guide rail is round and said trolley slips around the circumference of said guide rail.

3. The system as defined in claim 1, wherein said trolley comprises a wheel having a flanged peripheral portion which engages said arcuate portion of said periphery of said guide rail.

4. The system as defined in claim 1, wherein said trolley comprises a linear bearing.

5. The system as defined in claim 1, wherein said work surface is a computer keyboard.

6. The system as defined in claim 1, wherein the position of said cradle above the work surface is adjustable.

7. The system as defined in claim 6, wherein said horizontal rod is supported by first and second support rods, said first and second support rods being adjustable with respect to said work surface to position said horizontal rod at selectable heights above said work surface.

8. The system as defined in claim 7, wherein said first and second support rods are supported by first and second clamps applied to an edge of the work surface.

9. The system as defined in claim 7, wherein said first and second support rods are further adjustable with respect to said work surface to position said horizontal rod at first and second positions with respect to an edge of said work surface.

10. A system for supporting the hands of a user above a work surface such that the user can freely move the hands with respect to the work surface, said system comprising:

a first end support and a second end support positionable proximate to the work surface;

a guide rail horizontally disposed between said first end support and said second end support, said guide rail having an outer periphery, at least a top portion of said outer periphery being arcuate;

a first trolley and a second trolley positioned on said guide rail for horizontal movement thereon and for arcuate movement about said guide rail;

a first cradle suspended from said first trolley beneath said guide rail, said first cradle positioned to support the user's right hand, right wrist and a portion of the lower right arm above the work surface, said first cradle moving horizontally with horizontal movement of said first trolley, said first cradle moving arcuately with respect to said guide rail with arcuate movement of said first trolley about said guide rail; and a second cradle suspended from said second trolley beneath said guide rail, said second cradle positioned to support the user's left hand, left wrist and a portion of the lower left arm above the work surface, said second cradle moving horizontally with horizontal movement of said second trolley, said second cradle moving arcuately with respect to said guide rail with arcuate movement of said second trolley about said guide rail.

11. The system as defined in claim 10, wherein said guide rail is round and wherein said trolley rolls along the length of said guide rail and slides around the periphery of said guide rail.

12. The system as defined in claim 10, wherein the position of said first and second cradles above said work surface is adjustable.

13. The system as defined in claim 10, wherein the position of said first and second cradles with respect to an edge of said work surface is adjustable.

14. The system as defined in claim 10, wherein each of said first and second trolleys comprises a linear bearing positioned on said rod.

15. The system as defined in claim 10, wherein each of said first and second trolleys comprises a flanged wheel.

16. A system which supports the hands of a user above a work surface, comprising:

a first support and a second support positionable proximate to said work surface;

a horizontal guide rail supported at respective first and second ends by said first and second supports, said guide rail having an arcuate outer periphery;

a first trolley and a second trolley positioned on said guide rail in contact with said periphery of said guide rail, said first and second trolleys moveable along said guide rail and slidable about the periphery of said guide rail; and a first cradle suspended from said first trolley and a second cradle suspended from said second trolley, said first and second cradles moveable longitudinally below said guide rail and arcuately about said guide rail, each of said first and second cradles comprising a first portion to support a portion of the lower arm of a user and comprising a second portion extending from the first portion to support the wrist and hand of the user.

17. A system for supporting a hand of a user when performing manual tasks above a computer keyboard, comprising:

a horizontally disposed guide rail supported above the computer keyboard;

at least one trolley positioned on said guide rail, said trolley providing horizontal movement along said guide rail and providing arcuate movement about said guide rail; and a cradle suspended from said trolley, said cradle sized to support a portion of a user's hand, wrist and lower arm above said computer keyboard, said cradle having side portions to constrain a portion of the user's lower arm therebetween, said cradle having an extended forward portion to support the user's wrist and hand, said cradle permitting horizontal movement of the user's hand parallel to said guide rail and permitting arcuate movement of the user's hand around said guide rail.

* * * * *